United States Patent [19]

Bezzegh et al.

[11] Patent Number: 4,647,599

[45] Date of Patent: Mar. 3, 1987

[54] SUSTAINED RELEASE PHARMACEUTICAL TABLETS AND PROCESS FOR THE PREPARATION THEREOF

[75] Inventors: Dénes Bezzegh; Pál Fekete; Zoltán Toth; Ilona Bor; Erzsebet Fellner, all of Budapest, Hungary

[73] Assignee: Egyt Gyogyszervegyeszeti Cyar, Budapest, Hungary

[21] Appl. No.: 669,945

[22] Filed: Nov. 9, 1984

[30] Foreign Application Priority Data

Nov. 11, 1983 [HU] Hungary ............................. 3859/83

[51] Int. Cl.⁴ ........................... A61K 9/22; A61K 9/24
[52] U.S. Cl. .................................. 523/105; 424/470; 424/81; 514/777
[58] Field of Search ........................ 424/19, 22, 20; 514/777; 523/105

[56] References Cited

U.S. PATENT DOCUMENTS

| | | | |
|---|---|---|---|
| 2,909,462 | 10/1959 | Warfield et al. | 424/81 |
| 3,362,881 | 1/1968 | Eberhardt et al. | 424/19 |
| 3,458,622 | 7/1969 | Hill | 424/19 |
| 3,590,117 | 6/1971 | Christenson et al. | 424/19 |
| 3,634,584 | 1/1972 | Poole | 424/19 |
| 3,870,790 | 3/1975 | Lowey et al. | 424/19 |
| 4,252,786 | 2/1981 | Weiss et al. | 424/21 |
| 4,351,825 | 9/1982 | Sothmann et al. | 424/22 |
| 4,524,060 | 6/1985 | Mughal et al. | 424/22 |
| 4,557,925 | 12/1985 | Lindahl et al. | 424/19 |

*Primary Examiner*—Ronald W. Griffin
*Attorney, Agent, or Firm*—Keil & Weinkauf

[57] ABSTRACT

The invention provides a method for preparing sustained release tablets comprising a hydrophilic polymer matrix, which amounts to at least 10% by weight of the composition, consisting of a 5:1–1:5 weight to weight ratio mixture of a VP-VA copolymer and of an acrylic acid homopolymer, cross-linked with polyallyl saccharose.

The method of manufacturing of sustained release tablets according to the invention can be accomplished in two ways: either by manufacturing the granulate containing the active ingredient, or by supplementing the matrix granulate containing no active ingredient with the suitable amount of the active ingredient.

The latter variant involves the advantage of a possible separation of large-scale manufacturing of pharmacons and that of a generally applicable retardizing system, the composition and, consequently, the retardizing ability of which can optionally be modified in accordance with the properties of the active ingredient(s) to be formulated.

16 Claims, No Drawings

SUSTAINED RELEASE PHARMACEUTICAL TABLETS AND PROCESS FOR THE PREPARATION THEREOF

This invention relates to preparation of sustained release tablets, more particularly to tablets comprising a matrix consisting of a vinylpyrrolidone-vinylacetate (VP-VA) copolymer and of a polyacrylate cross-linked with polyallyl saccharose, and to a process for the preparation thereof.

Tablets with prolonged active ingredient release profile of the hydrophilic matrix type form a significant group of compositions with sustained release of the active ingredient. If water-soluble high molecular weight polymers or mixtures thereof are applied as matrix forming components, more simple compositions of a less even release profile are obtained. U.S. Pat. No. 3,362,881 discloses among others the use of carboxymethyl cellulose sodium (CMC-Na) and of polyacrylic acid, while in U.S. Pat. Nos. 3,590,117 and 3,870,790 the use of several cellulose derivatives (e.g. hydroxypropyl cellulose, hydroxypropylmethyl cellulose, CMC, and the mixtures thereof) is suggested for the same purpose.

Compositions wherein the matrix is made from polymers being water-soluble per se but able to form a rubber-like, water-insoluble complex when reacting with each other in an aqueous medium, provide a more even release of the active ingredient. Such compositions are described in U.S. Pat. Nos. 3,458,622 and 3,634,584 proposing the polyacrylic acid cross-linked with polyallyl saccharose as the "acidic" component of the matrix forming complex. These polymers may be prepared by the method described in U.S. Pat. No. 2,909,462 and are marketed by B. F. Goodrich Chemical Co. under trade names Carbopol 934, 940 and 941. As "basic" components forming the water-insoluble complex in the aqueous medium with the aforementioned "acidic" component the use of polyvinylpyrrolidone (PVP) is mentioned in U.S. Pat. No. 3,458,622, while in U.S. Pat. No. 3,634,584 polyoxyethylene type polymers are referred to.

Although those tablets whose matrices are built up from such complexes are superior to "simple" hydrophilic matrix tablets in respect of their active ingredient releasing capacity being independent of the pH of the aqueous medium, or in vivo that of the gastrointestinal tract, respectively, and their active ingredient release being fairly even, but the drawback still exists—which applies similarly to all hydrophilic matrix tablets—that the matrix capable of retarding the dissolution of the active ingredient is formed only when the solvent medium penetrates into the tablet. Thus the initial release of the active ingredient is quite rapid (being usually over 40% in the first hour).

The aforementioned drawback can be overcome by using the method described in Hungarian Pat. No. 175,540 comprising the application of a film-coating onto the surface of the tablets. This film-coating consists of water-soluble and water-insoluble polymers. The coating itself is dissolved only slowly in aqueous medium, while it acts as a semipermeable membrane as long as its dissolution proceeds. This semipermeable membrane behaviour means that only water is allowed to diffuse inside the matrix, while the liberation of the active ingredient is inhibited. Thus until the formation of the water-insoluble complex is under way, the release of the active ingredient will be retarded by the barrier effect of the film-coating.

The main problem accompanying the preparation of hydrophilic matrix tablets based on complex formation is to provide a granulate with appropriate grain size and to assure its suitability of being compressed into tablets. According to known methods the complex granulate comprising active ingredient(s) can be produced by the so-called dry granulation process. In this procedure the complex forming polymers, the active ingredients and—optionally—other auxiliary agents are blended to form a powder, then the mixture is subjected to pressing or briquetting, and finally the granulate is obtained by grinding.

As it is stated in the Hungarian Pat. No. 175,540, the wet granulation process, most widespreadly used in today's pharmaceutical industrial practice, cannot favourably be applied to prepare the matrix granulate. In this procedure the powdery mixture containing the components of the matrix, the active ingredient(s) and optionally other adjuvants is moistened with a granulating liquid, e.g. dichloromethane, chloroform, dichloroethane, trichloroethylene, ethanol or isopropanol, or by using a solution containing any of the above solvents, and a binder, for example ethyl cellulose, shellac, as a solute. After having kneaded together the ingredients of the mixture, the resulting mass is rubbed through a sieve of appropriate mesh size, then subjected to drying. The dried mass is repeatedly sieved. The drawback of this process is that the complex formed also when kneading the powder mixture with the alcohols, mentioned hereinabove, makes the dispersing of the wet aggregates (i.e. when rubbing the wet mass through the sieve) difficult. On the other hand, the use of chlorinated hydrocarbon solvents, which are known to be inert in respect of complex formation, constitutes considerable environmental risks and harmful effects to the health of the persons in contact with these solvents.

A further disadvantage of the tablets containing PVP as "basic" component can be attributed to the strong hygroscopic nature of PVP, resulting in poor storage stability of the tablets under more humid environments. (In an atmosphere characterized by more than 75 p.c. of relative humidity the stability of these tablets proved to be unsatisfactory: their surface tends to become sticky and the outer appearance unpleasing.)

The object of the present invention is to overcome the above difficulties, by means of improving the steadiness of the active ingredient release, by reducing it in the first hour after ingestion, and also by developing a readily reproducible wet granulation technique to prepare the matrix granulate, and additionally, by improving the storage stability of the tablets under more humid environments.

It has been found in an unforeseen manner that matrix tablets of pronounced advantageous properties can be prepared, even on industrial scale, by using Carbopol 934 type acrylic acid polymer as "acidic" component, together with a vinylpyrrolidone-vinylacetate copolymer, as the "basic" component of the matrix, and by carrying out granulation by means of an aliphatic alcohol, preferably isopropanol, in the presence of a "basic" component and of a waxy substance, applying a fluidized bed granulation technique, preferably. The waxy substance used as granulation additive according to the invention may be a long-chain aliphatic alcohol, a fatty acid or an ester thereof, and a mixture of the same.

The "basic" component of the matrix according to the invention contains 60% by weight of vinylpyrrolidone and 40% by weight of vinylacetate.

These percentages refer to the composition of the starting monomeric mixture. The number K, characterizing the progress of the polymerization, is about 30. For example, vinylpyrrolidones, e.g. under the trade name "Plasdone VA 630" of General Aniline and Film Co., and vinylacetates, e.g. those marketed with trade names "Kollidon VA 64" or "Luviskol VA 64", both from Badische Anilin und Sodafabrik AG, are applicable with good results.

The binding material used in the alcoholic solution for granulation may be the VP-VA copolymer per se, mentioned hereinabove, or a polyoxyethylene (called also polyethylene glycol), e.g. those with the trade name "Carbowax", further PVP, a hydroxycellulose—for example hydroxypropylcellulose, marketed under trade name "Klucel LF", or hydroxypropylmethylcellulose, marketed by the name "Methocel E50", or hydroxyethylcellulose, known by trade name "Tylose", etc.—can also be used.

The alcoholic solution applied for granulation should, in addition to the "basic" complex forming ingredient, contain 0,5 to 10% by weight of a waxy substance, calculated on the amount of starting materials, in order to improve the granulability. For this purpose fats, fatty acids, fatty alcohols, or esters of fatty acids with lower alkanols, i.e. with those containing 1 to 3 carbon atoms, possessing an appropriate solubility in the alcohol used, may be applied, so e.g. hydrogenated castor-oil, stearic acid, cetylalcohol, cetylstearylalcohol, isopropyl palmitate, etc. In order to facilitate the dissolution of the added waxy substance, the solution may eventually be warmed up to about 40° to 60° C.

The ratio of "acidic" to "basic" components used to build up the matrix can optionally be in the range of 5:1 to 1:5; the 1:1 ratio is, however, preferable. The amount of the "basic" polymer dissolved in the solution for granulation can be 0.5 to 10% by weight, calculated on the total weight of the composition. An amount between 2% and 6% is preferred. The amount of complex forming polymers should be of at least 10% by weight, calculated on the total weight of the tablet. The matrix comprising the active substance(s), the complex forming polymers and the granulation adjuvant(s) may additionally contain filling material(s) usually applied in the manufacturing of pharmaceutical tablets. The amount of the filling materials may range from 0% to 79% by weight of the tablets. Lactose, microcrystalline cellulose or polyvinylbutyral (marketed by trade name "Mowital 30T") are preferred examples of these filling materials. The weight of the ready-for-use tablets may reach 1 g as a maximum; tablets weighing less than 0.75 g may, however, be applied advantageously, considering the ease of the ingestion of tablets.

The process described hereinabove is suitable for manufacturing orally administered sustained release tablets comprising a wide range of active ingredients. The actual composition of the tablets may vary of course—as a consequence of the different doses of the active substances and due to their divergent physical properties—but the preferred composition of the tablet, assuring an even release profile of the active ingredient, is easy to determine for a person skilled in the art, by a small number of experiments, following the above guidance.

Examples of pharmaceutically active substances which can preferably be used in the process according to the present invention are as follows: glycerol trinitrate, N-(p-chlorobenzyl)-N-(2-pyridyl)-N',N'-dimethylethylenediamine(chloropyramine), pyridine-2-carboxylic acid-(4-benzyl)-piperazide(piberaline), N-($\alpha$)-benzylcarbamoyl-ethyl-isonicotinic hydrazide(nialamide), (+,−)(1-isopropylamino-3-p-(2-methoxyethyl)-phenoxy)-2-propanol(metoprolol), 5-(3-dimethylamino-2-methylpropyl)-10,11-dihydro/5H/-dibenzo/b,-b/azepine(trimipramine), 2-methylthio-10-(2-(1-methyl-2-piperidyl)-ethyl)-phenothiazine(thioridazine), 5-(3-dimethylaminopropyl)-10,11-dihydro/5H/-dibenzo/b,-b/azepine(imipramine), 2,4-diamino-5-(3',4',5'-trimethoxybenzyl)-pyrimidine(trimethoprim), 2-ethylthio-10-(3-(4-methyl-1-piperazinyl)-propyl)-phenothiazine(-thietilperazine), 1-(3,5-dihydroxyphenyl)-2-(tert-butylamino)-ethanol(terbutaline), 2-(2-(1-(4-chlorophenyl)-1-phenyl-ethoxy)ethyl)-1-methylpyrrolidine(-clemastine), N,N-dimethyl-3-((1-phenylmethyl)-cycloheptyloxy)-propanamine(bencyclan, 1-(1H-indol-4-yloxy)-3-((1-methylethyl)amino)-2-propanol(pindolol), 2-amino-3,5-dibromo-N-cyclohexyl-N-methyl-benzylamine(bromhexine), 3-aminosulphonyl-4-chloro-N-(2,6-dimethyl-1-piperidinyl)-benzamide(clopamide), N,N-dimethyl-3-(dibenzo/c,d/cycloheptadiene-5-ylidene)-propylamine(amitriptyline), 2-methyl-2n-propyl-trimethylene-dicarbamate(meprobamate), 1-(3,4-dimethoxyphenyl)-5-ethyl-7,8-dimethoxy-4-methyl-/5H/-2,3-benzodiazepine(tofizopam), acetylsalicylic acid, 4-hydroxy-acetanilide(paracetamol), chinidine sulfate, iron sulfate, theophylline, (−)-3-(3,4-dihydroxyphenyl)-2-methyl-alanine(methyldopa), etc. (The respective International Non-proprietary Names accepted by the WHO are shown in parentheses.)

The advantageous caharacteristics over prior art, attainable by applying the method of granulation and following the instructions regarding the composition of tablets, described in the present invention—i.e. the improved steadiness of active substance release, the safe moist granulation procedure that can be used on industrial scale, and the better storage stability of the tablets—may be explained by the following hypothesis, without limiting the scope of protection to the said theory.

The more even release of the active ingredient, more exactly the decrease of the initial speed of its release, is probably caused by the fact that the granulation is carried out by using a solution containing the "basic" component of the matrix forming polymer mixture, and therefore a film-coating is formed around the particles of the "acidic" component. This coating, affected by the solvent medium, dissolves more rapidly and reacts by a greater speed and uniformity with the surface layers of the "acidic" polymer particles, when compared to other granulation techniques, wherein the particles of the two matrix forming polymers are present as a mere physical mixture in matrix.

The facilitation of the moist granulation process is made possible by using a VP-VA copolymer, in addition to the waxy substance dissolved in the liquid for granulation. As a consequence of the use of these substances, complex formation in the course of the granulation process occurs only to a limited extent (as compared to the use of PVP per se); while in case of applying kneading during the manufacturing process, the sieving of the wet aggregates becomes facilitated, and, on the other hand, using a fluidized bed granulation technique, the formation of too large granules (e.g. of some cm-s in diam.) can be avoided.

According to the present invention, the granulation of the powder mixture can be accomplished even if the mixture does not contain active ingredient or inert filling material, either. Thus, following the method described hereinbelow, a placebo granulate, consisting of the matrix formed through complex formation, may also be prepared. To prepare lower dosage forms having an active ingredient content below 100 mg., addition of the active ingredient in powdered form to the placebo granulate may be accomplished. In this way, the sustained release composition aimed at may readily be obtained.

The better storage stability can also be attributed to the effect of the VP-VA copolymer; the latter exhibits a considerable lower hygroscopicity than the PVP, predominantly used in the practice so far. Therefore, the tablets can be stored even in atmospheres of higher humidity content. (According to data from BASF Co., the producer of these polymers, at 75 p.c. relative humidity level, the water-absorbing capacity of vinylpyrrolidone homopolymers is about 28%, while that of Luviskol VA 64, a VP-VA copolymer with 40 p.c. of VA-content, reaches only 17%. The respective figures at 90 p.c. relative humidity are: 60% and 38%. Source: Technisches Merkblatt Luviskol VA-Marken, Badische Anilin und Sodafabrik AG, June 1972.)

The outstanding features of the preparates according to the invention, in relation to hygroscopicity, are demonstrated by the data shown on Table 1. The matrix granulates prepared according to Example 3 were subjected to pressing—with or without admixing glycerol trinitrate impregnated lactose—to form tablets of 6 cm diam. and 80 mg. weight. Drying losses of the tablets had been determined, then the tablets were placed into open containers surrounded by an atmosphere of 75 p.c. or 90 p.c equilibrium humidity, respectively. Weight gains were successively measured until equilibrium moisture contents have been reached. Water absorbing capacity of the compositions has been evaluated by determining their respective equilibrium moisture content. The results obtained are shown on Tables 1 and 2.

TABLE 1

Comparison of water absorbing capacity of placebo preparates containing PVP or Luviskol, respectively

| | Initial moisture content | Equilibrium values in a room | |
|---|---|---|---|
| | | of 75 p.c. rel. humidity | of 90 p.c. rel. humidity |
| Matrix tablets containing PVP | 7.4% | 17.3% | 22.7% |
| Matrix tablets containing Luviskol | 3.8% | 13.4% | 19.8% |

Drying losses were measured at 105 C.°, 2 hours.

TABLE 2

Comparison of water absorbing capacity of tablets containing glycerol trinitrate active ingredient and PVP or Luviskol as matrix forming polymers, respectively

| | Initial moisture content | Equilibrium values in a room | |
|---|---|---|---|
| | | of 75 p.c. rel. humidity | of 90 p.c. rel. humidity |
| Tablets containing PVP | 3.8% | 9.1% | 14.2% |

TABLE 2-continued

Comparison of water absorbing capacity of tablets containing glycerol trinitrate active ingredient and PVP or Luviskol as matrix forming polymers, respectively

| | Initial moisture content | Equilibrium values in a room | |
|---|---|---|---|
| | | of 75 p.c. rel. humidity | of 90 p.c. rel. humidity |
| Tablets containing Luviskol | 2.1% | 7.8% | 11.5% |

Drying losses were measured at 80 C.°, 3 hours.

The present invention therefore provides a process for the manufacturing of controlled-release tablets, containing 800 mg of active ingredient as a maximum, by applying wet granulation, preferably fluidized bed granulation, technique. The method according to the invention comprises the use of a 5:1 to 1:5 weight to weight ratio mixture of a VP-VA copolymer and of polyacrylic acid, cross-linked with polyallylsaccharose, and—if desired—also the application of inert filling materials. Furthermore it includes the use of a liquid for granulation containing a polymer that forms a water-insoluble complex with polyacrylic acid in aqueous medium and a waxy substance, and a $C_{1-5}$ alkanol as solvent. The process can be realized essentially in two ways: either matrix granulates containing the active ingredient(s) are prepared, or the latter are added to the granulate containing no active ingredient, in a separate step.

The controlled release tablets prepared according to the invention exhibit more even active ingredient release properties and reduced water absorbing capacities as compared to similar type tablets, and the polymers used in the manufacture of the granulates do not form clusters, this being a further technological advantage.

The present invention is further demonstrated by means of comparative examples. The examples emphasize the favourable characteristics of the process according to the invention, without limiting its scope to the subject matter disclosed actually in the examples. The advantageous features involved in the process according to the invention are as follows:

the "basic" complex forming component favourably affects the speed of dissolution of the active ingredient the process is applicable for a wide range of active ingredients which differ considerably from each other regarding their physical parameters.

The following examples refer to the manufacturing of preparates comprising the compounds listed below as active ingredients, revealing a suitable method for the preparation of placebo tablets as well.

The following pharmakons were formulated to tablets by using the method of invention: N-(p-chlorobenzyl)-N-(2-pyridyl)-N',N'-dimethylethylenediamine(-chloropyramine); glycerol trinitrate; N,N-dimethyl-3-((1-phenylmethyl)-cycloheptyloxy)-propanamine (bencyclan); pyridine-2-carboxylic acid-(4-benzyl)-piperazide(piberaline); iron sulfate+ascorbic acid.

EXAMPLE 1

Preparation of Tablets Containing Chloropyramine Hydrochloride as Active Ingredient Into the pan of a fluidization-spraying granulator equipment, type "Glatt WSG 1", the following amounts of materials were introduced:

chloropyramine hydrochloride: 700 g

Carbopol 934: 350 g
Luviskol VA 64: 350 g

Granulation was carried out by using solutions, the compositions of which are indicated in Table 3.

TABLE 3

Preparation of chloropyramine · HCl tablets by varying the granulation additives

| | Number of the experiment | | |
|---|---|---|---|
| Granulation additives | 1 (according to invention) | 2 (references) | 3 |
| Isopropanol | 600 ml | 600 ml | 600 ml |
| Stearic acid | 50 g | 50 g | none |
| Polyethyleneglycol* | 50 g | none | none |
| Hydroxypropyl cellulose** | 50 g | none | none |

*Carbowax 6000;
**Klucel LF

Granulation conditions: temperature of the fluidizing air: 25 C.°; dosage rate of the granulation liquid: 25 ml/min; spraying pressure: 0.5 bar (=50 kPa).

In course of Experiment 3 we failed to prepare a granulate suitable for further processing, since due to the isopropanol injection, not a granulate containing grains of size of approximately a few tenth mm was formed, as expected, but aggregates of a few cm-s in size have been obtained. To the granulates prepared in Experiments 1 and 2, 1% of magnesium stearate and 2% of talc were admixed; the homogenates were then processed by a rotary tablet-machine, type "Fette EXI", provided with a flat-faced pressing tool of 8 mm $\phi$, by exerting a pressing force of 15,000 Newton. As a result tablets weighing a total of 0.17 gram, containing 75 mg of chloropyramine hydrochloride, were obtained. Active ingredient release was determined by using a disintegration testing apparatus according to USP XX. 0.1N hydrochloric acid was applied as test medium and a constant temperature of 37 C.° was kept during the test.

700 ml of extracting liquid was filled to the extracting chamber of the device and six tablets were put into the extraction basket. The tablets were agitated in the extracting liquid by moving the basket in the medium in a standard, predetermined way. The test medium was sampled every hour; active substance contents of the samples were determined spectrophotometrically. The active substance contents measured over a period of 7 hour, characterising the release profile, are shown in the following Table 4.

TABLE 4

Dynamics of active ingredient release

| Extraction time (hours) | Experiment 1 (Tablet prepared according to invention) | Experiment 2 (reference) |
|---|---|---|
| 1 | 23.8% | 38.8% |
| 2 | 41.0% | 60.9% |
| 3 | 54.2% | 80.6% |
| 4 | 66.6% | 86.5% |
| 5 | 79.7% | 93.5% |
| 6 | 87.7% | 98.0% |
| 7 | 92.5% | — |

EXAMPLE 2

Preparation of Placebo Granulate

Applying the fluidization-granulation method described in Example 1, the following placebo matrix granulates were prepared:

| | Number of the experiment | | | | |
|---|---|---|---|---|---|
| | 1 | 2 | 3 | 4 | 5 |
| Composition of powder mixtures to be granulated | | | | | |
| Ingredients | | | | | |
| Luviskol VA 64 | 750 g | 750 g | 450 g | 450 g | 450 g |
| Carbopol 934 | 750 g | 750 g | 450 g | 450 g | 450 g |
| Avicel PH 101 | — | — | 600 g | — | — |
| Lactose | — | — | — | 600 g | — |
| Mowital B30T | — | — | — | — | 600 g |
| Composition of the granulating solutions | | | | | |
| Components | | | | | |
| Isopropanol | 800 ml | 800 ml | 800 ml | 800 ml | 800 ml |
| Luviskol VA 64 | — | 150 g | 150 g | 150 g | 150 g |
| Stearine | 50 g | 50 g | — | 50 g | — |
| Cetylstearyl alcohol | — | — | 50 g | — | 50 g |

In Experiment 1 granulating solution did not contain any "basic" complex forming polymer; this experiment serves as comparison when evaluating experiments Nos. 2–5, carried out according to the present invention.

Having added lactose with a 10% glycerol trinitrate content, and lubricants to the placebo granulate mixture produced as described above, the powder mixtures 1 to 5 of Experiment 2 were further processed to obtain tablets of 80 mg weight and 6 mm $\phi$, each containing 2.5 mg of glycerol trinitrate.

The release of the active ingredient from the tablets was investigated by the "half-change" method using a disintegration testing apparatus according to USP XX. Into the container of the apparatus 700 ml of artificial gastric fluid was introduced and 6 tablets of each experiment were put into the extraction basket. The half of the dissolving medium was replaced each hour by artificial intestinal fluid. Release of glycerol trinitrate from the tablets was monitored by spectrophotometric assay of metabolites formed through hydrolysis in the basic medium.

Results of the dissolution experiments are summarized in the following table:

| Time (hours) | pH of the solution | No. of the experiment | | | | |
|---|---|---|---|---|---|---|
| | | 1 | 2 | 3 | 4 | 5 |
| 1 | 1.1 | 37.3% | 26.9% | 32.1% | 31.1% | 20.5% |
| 2 | 2.1 | 40.0% | 32.1% | 44.6% | 40.4% | 30.8% |
| 3 | 5.5 | 62.8% | 39.4% | 55.0% | 61.1% | 40.1% |
| 4 | 6.3 | 83.2% | 48.2% | 61.2% | 78.7% | 56.7% |
| 5 | 6.7 | 100% | 58.7% | 67.4% | 96.8% | 67.0% |
| 6 | 7.0 | | 70.6% | 73.6% | | 74.3% |
| 7 | 7.2 | | 75.0% | 79.8% | | 83.6% |
| 8 | 7.2 | | 83.6% | 86.1% | | 89.0% |

EXAMPLE 3

Preparation of Sustained Release Tablets Containing Glycerol Trinitrate Active Ingredient Into the container of a fluid bed spray granulator model WSG 120, Fa. W. Glatt, Haltingen, FRG, 25.0 kg of Luviskol VA 64 and the same amount of Carbopol 934 were introduced, then the powder mixture was subjected to granulation by using a solution comprising 32 kg of isopropanol, 2.7 g of stearic acid and 2.7 kg of "Carbowax 6000". The rate of injection of the granulation liquid was adjusted to 1000 ml/min; the spraying pressure was as high as 3 bar, the air velocity in the fluidization chamber was set between 1000 and 1200 m³/hour, temperature of inlet air was 40 C.°. The granulate was dried to 4% moisture content, followed by homogenization with lactose, containing 10% added glycerol trinitrate, according to Experiment 2. The homogenate was compressed into tablets of 80 mg weight, 6 mm diameter, each containing 2.5 mg of glycerol trinitrate. Release of the active ingredient was successively measured by the "half-change" method according to Example 1. The amounts of glycerol trinitrate dissolved from the tablets within 8 hours are expressed in percentages of the initial active ingredient content and shown in the following table:

| 1 h | 2 h | 3 h | 4 h | 5 h | 6 h | 7 h | 8 h |
|---|---|---|---|---|---|---|---|
| 21.1% | 29.9% | 46.6% | 60.7% | 73.4% | 91.0% | 100% | — |

EXAMPLE 4

Preparation of Tablets Containing Bencyclan as Active Ingredient 200 parts of bencyclan fumarate, 57.5 parts of Kollidon VA 64 and 57.5 parts of Carbopol 934 were weighed and intensively blended together. The powder mixture then was moistened with a solution containing 9 parts of Carbowax 6000 and 9 parts of stearic acid in 80 parts of isopropanol. (All parts here are to be understood as weight parts.) The wet aggregates were rubbed through a sieve of 20 mesh, dried, and sifted again. 7 parts of magnesium stearate together with 10 parts of talc were then admixed. The homogenate was compressed into tablets of 350 mg weight, 10 mm $\phi$, each containing 200 mg of active substance. Release of the active ingredient was studied by the "half-change" method using a disintegration testing apparatus according to USP XX. The following results were obtained:

| 1 h | 2 h | 3 h | 4 h | 5 h | 6 h | 7 h | 8 h |
|---|---|---|---|---|---|---|---|
| 30.0% | 42.4% | 44.7% | 50.7% | 59.0% | 68.7% | 77.4% | 84.8% |

EXAMPLE 5

Preparation of Tablets Containing Piberaline as Active Ingredient 80 parts by weight of piberaline, 33.6 parts of Plasdone VA 630 and 33.6 parts of Carbopol 934 were mixed together, followed by moistening with a solution comprising 3.2 parts of Carbowax 6000, 1.6 parts of stearic acid and 50 parts of ethanol. (The term "parts" here—if not otherwise stated—refer to weight parts.) The wet aggregates were rubbed first through a sieve of 16 mesh, then, after drying having been completed, through a second sieve of 20 mesh. 4.8 parts of talc and 3.2 parts of magnesium stearate were admixed. Tablets of 160 mg weight, 8 mm diameter, containing 80 mg active ingredient were obtained by pressing.

Release of the active ingredient was followed by the "half-change" method as described in Example 1. The following values have been measured within 8 hours test time:

| 1 h | 2 h | 3 h | 4 h | 5 h | 6 h | 7 h | 8 h |
|---|---|---|---|---|---|---|---|
| 31.8% | 44.3% | 53.8% | 61.8% | 70.5% | 79.4% | 84.5% | 92.0% |

EXAMPLE 6

Preparation of Tablets Containing Iron Sulfate and Ascorbic Acid as Active Ingredients To 1.00 kg of placebo matrix granulate prepared according to Example 3 3.20 kg of $FeSO_4.1.5H_2O$, 0.20 kg of Mowital B30T (a brand of polyvinylbutyral), 0.40 kg of ascorbic acid (Vitamin C), 0.15 kg of talc and 0.05 kg of magnesium stearate were admixed. The homogenate was further processed to tablets of 500 mg weight, 12 mm $\phi$, each tablet containing 100 mg of $Fe^{++}$ and 40 mg of ascorbic acid, by using a rotary-type granulator model Manesty B3B. Dissolution of $Fe^{2+}$ from the tablets was investigated by the "half-change" method in a disintegration testing apparatus equipped with a paddle, according to USP XX, at 100 r.p.m. The following table contains data characterizing the release of iron from the composition:

| 1 h | 2 h | 3 h | 4 h | 5 h | 6 h |
|---|---|---|---|---|---|
| 42.4% | 62.2% | 75.0% | 79.5% | 82.5% | 85.5% |

EXAMPLE 7

Preparation of Sustained Release Tablets Containing Imipramine Hydrochloride as Active Ingredient 100.0 g of imipramine hydrochloride, 75.0 g of Luviskol VA 64, and 75.0 g of Carbopol 934 were intimately blended, and the resulting mixture homogenized. The homogenate was moistened thoroughly with a solution comprising:

5.0 g of Carbowax 6000 /polyoxyethyleneglycol/
5.0 g of stearic acid and
60.0 ml of isopropanol;
at a temperature of 40 C.°.

The wet mass was rubbed through an 18 mesh stainless steel sieve, followed by drying the wet granulate at 40 C.°, until its moisture content was below 1%. The obtained dry granulate was regranulated and blended with 6.0 g of talc and 4.0 g of magnesium stearate, followed by homogenization of the resulting mixture. The final granulate so obtained was further processed by pressing to give tablets of 0.135 g weight, 7 mm diam.

Liberation of the active ingredient from these tablets was monitored by using the half-change method as described in Example 2. The results are presented on the following table:

| 1 hour | 2 hour | 3 hour | 4 hour | 5 hour | 6 hour |
|---|---|---|---|---|---|
| 30-35% | 45-55% | 55-65% | 65-75% | 75-85% | 85-95%. |

The above percentages refer to the relative amounts of active ingredient liberated until a pre-set time had elapsed, in different experiments, and represent end values.

EXAMPLE 8

Preparation of Sustained Release Tablets Containing Theophylline as Active Ingredient According to Experiment 4 of Example 2, a matrix granulate containing no active ingredient was prepared, by using of which the following composition was made:

| | | |
|---|---|---|
| theophylline | 200.0 g | |
| matrix granulate | 117.5 g | |
| Carbowax 6000 | 15.0 g | |
| magnesium stearate | 7.0 g | |
| talc | 10.5 g | |
| | 350.0 g | |

The powder mixture was subjected to pressing to give tablets of 0.350 g weight and 10 mm diam. each. Dynamics of the dissolution of the active ingredient as measured by the half-change method are characterized by the data presented below:

| 1 h | 2 h | 3 h | 4 h | 5 h | 6 h |
|---|---|---|---|---|---|
| 20–25% | 28–33% | 34–40% | 50–55% | 65–70% | 80–90%. |

What we claim is:

1. A process for preparing sustained release tablets, containing not more than 800 mg of active ingredient, by means of a wet granulation method, characterized in that a 5:1 to 1:5 weight to weight ratio mixture of (a) a vinylpyrrolidone-vinylacetate copolymer and (b) an acrylic acid polymer, cross-linked with polyallylsaccharose, is used in an amount of at least 10% by weight of the composition, and that a granulating solution, comprising a polymer which forms a water-insoluble complex with the acrylic acid polymer in aqueous medium and 0.5 to 10% by weight of a waxy substance as solutes, and a $C_{1-5}$ alkanol as solvent, is applied, either to prepare directly a granulate containing the active ingredient, or by admixing the active ingredient with the granulate, prepared previously without any active ingredient, in a separate step.

2. A process according to claim 1, characterized in that the said copolymer consists of 60% of vinylpyrrolidone and 40% of vinylacetate.

3. A process according to claim 1, characterized in that an isopropanolic solution is applied for granulation, containing 0.5% to 10% of VP-VA copolymer and/or polyoxyethylene, and further 0.5% to 10% of stearic acid and/or cetylstearyl alcohol, by weight, related to the total weight of the tablet.

4. A process according to claim 1, characterized in that microcrystalline cellulose and/or polyvinylbutyral is applied as inert auxiliary agent(s).

5. A process according to claim 1, characterized in that N-(p-chlorobenzyl)-N-(2-pyridyl)-N,N'-dimethylethylenediamine is used as active ingredient.

6. A process according to any of claims 1 to 4, characterized in that glycerol trinitrate is used as active ingredient.

7. A process according to any of claims 1 to 4, characterized in that N,N-dimethyl-3-((1-phenylmethyl)-cycloheptyloxy)-propanamine is used as active ingredient.

8. A process according to any of claims 1 to 4, characterized in that pyridine-2-carboxylic acid-(4-benzyl)-piperazide is used as active ingredient.

9. A process according to any of claims 1 to 4, characterized in that ferrous sulfate is applied as active ingredient.

10. A process according to any of claims 1 to 4, characterized in that 5-(3-dimethylaminopropyl)-10,11-dihydro/5H/-dibenzo(b,b)azepine is applied as active ingredient.

11. A process according to any of claims 1 to 4, characterized in that teophylline is applied as active ingredient.

12. A process according to claim 1 characterized in that said wet granulation is fluidized bed granulation.

13. A process according to claim 1 characterized in that an inert filling material is used in said composition.

14. Tablet of sustained active ingredient release containing not more then 800 mg of active ingredient and in a 5:1 to 1:5 weight to weight ratio a mixture of a vinylpyyrolidone-vinylacetate copolymer and an acrylic acid polymer, cross-linked with polyallylsaccharose, wherein the amount of the said mixture is at least 10% by weight of the tablet.

15. A matrix (placebo) granulate, containing no active ingredient, comprising a 5:1 to 1:5 weight to weight ratio mixture of a vinylpyrrolidone-vinylacetate copolymer and an acrylic acid polymer, cross-linked with polyallylsaccharose.

16. A matrix (placebo) granulate according to claim 15 wherein an inert filling material is present.

* * * * *